(12) United States Patent
Lee (10) Patent No.: US 10,439,353 B2
(45) Date of Patent: Oct. 8, 2019

(54) LASER APPARATUS

(71) Applicant: LUTRONIC CORPORATION, Goyang (KR)

(72) Inventor: Hee Chul Lee, Goyang (KR)

(73) Assignee: LUTRONIC CORPORATION, Goyang (KR)

( * ) Notice: Subject to any disclaimer, the term of this patent is extended or adjusted under 35 U.S.C. 154(b) by 0 days.

(21) Appl. No.: 15/558,980

(22) PCT Filed: Mar. 17, 2016

(86) PCT No.: PCT/KR2016/002729
§ 371 (c)(1),
(2) Date: Sep. 15, 2017

(87) PCT Pub. No.: WO2016/148529
PCT Pub. Date: Sep. 22, 2016

(65) Prior Publication Data
US 2018/0248330 A1    Aug. 30, 2018

(30) Foreign Application Priority Data

Mar. 17, 2015   (KR) .................. 10-2015-0036788

(51) Int. Cl.
*H01S 3/10* (2006.01)
*H01S 3/08* (2006.01)
(Continued)

(52) U.S. Cl.
CPC .......... *H01S 3/08054* (2013.01); *A61B 18/22* (2013.01); *H01S 3/0615* (2013.01);
(Continued)

(58) Field of Classification Search
CPC ...... H01S 3/08054; H01S 3/0615; H01S 3/11; H01S 3/1611; H01S 3/1623;
(Continued)

(56) References Cited

U.S. PATENT DOCUMENTS 5,130,995 A *  7/1992  Grossman ............... H01S 3/117
                                                          372/107
8,275,015 B2 *  9/2012  Li ........................ H01S 3/0606
                                                           372/66

(Continued)

FOREIGN PATENT DOCUMENTS

| KR | 10-2012-0138182 A | 12/2012 |
| KR | 10-2013-010964 A | 10/2013 |
| KR | 10-2013-0114299 A | 10/2013 |

OTHER PUBLICATIONS

International Search Report for International Patent Application No. PCT/KR2016/002729 filed Mar. 17, 2016.

*Primary Examiner* — Kinam Park (57) ABSTRACT

A laser apparatus according to the present invention may comprise: a plurality of reflection mirrors which form a resonance path so as for light to be amplified by an induced emission; a medium having a first surface which forms a vertical surface with respect to the resonance path, and a second interface which does not form a vertical surface with respect to the resonance path, and absorbs energy from a light source and amplifies and emits the light; and a saturable absorber having a second surface which forms a vertical surface with respect to the resonance path, and a second interface which does not form a vertical surface with respect to the resonance path, and generates ultrashort pulses. The laser apparatus according to the present invention has the effects of cutting a saturable absorber having a specific crystallographic axis to thereby make polarization capacity in one direction advantageous and minimize propagation loss. In addition, the laser apparatus according to the present invention has the effect of maximizing transmittivity maintenance capacity of polarization orientation in one direction by arranging a medium and a saturable medium so as to have a specific inclined plane.

9 Claims, 7 Drawing Sheets

(51) Int. Cl.
H01S 3/11 (2006.01)
H01S 3/13 (2006.01)
H01S 3/06 (2006.01)
H01S 3/16 (2006.01)
A61B 18/22 (2006.01)
H01S 3/113 (2006.01)
H01S 3/092 (2006.01)
A61N 5/06 (2006.01)
A61N 5/067 (2006.01)
A61N 5/073 (2006.01)
A61B 18/20 (2006.01)

(52) U.S. Cl.
CPC ...... *H01S 3/08036* (2013.01); *H01S 3/10061* (2013.01); *H01S 3/11* (2013.01); *H01S 3/113* (2013.01); *H01S 3/1115* (2013.01); *H01S 3/1308* (2013.01); *H01S 3/1623* (2013.01); *A61B 2018/20553* (2017.05); *A61N 2005/067* (2013.01); *A61N 2005/0665* (2013.01); *A61N 2005/073* (2013.01); *H01S 3/092* (2013.01); *H01S 3/1611* (2013.01); *H01S 3/1643* (2013.01)

(58) Field of Classification Search
CPC ...... H01S 3/1643; H01S 3/1115; H01S 3/092; H01S 3/08036; H01S 3/10061; H01S 3/1308; H01S 3/113
See application file for complete search history.

(56) References Cited

U.S. PATENT DOCUMENTS

| | | | |
|---|---|---|---|
| 2005/0078719 A1* | 4/2005 | Masuda | H01S 3/0627 372/29.02 |
| 2011/0158267 A1* | 6/2011 | Tsai | H01S 3/0675 372/11 |
| 2013/0287051 A1* | 10/2013 | Kim | H01S 3/13 372/25 |
| 2015/0016484 A1* | 1/2015 | Kuramoto | H01S 3/0627 372/75 |

* cited by examiner

LASER APPARATUS

This application is a U.S. National Stage of PCT/KR2016/002729, filed Mar. 17, 2016, which claims the priority benefit of Korean Patent Application No. 10-2015-0036788, filed on Mar. 17, 2015 in the Korean Intellectual Property Office, the disclosures of which are incorporated herein by reference.

TECHNICAL FIELD

The present invention relates to a laser apparatus, and more specifically to a laser apparatus which splits polarization and maintains maintenance capacity of the split polarization by use of a medium, which generates a laser beam, a crystal structure of a saturable absorber, and an inclined plane.

BACKGROUND ART

A laser apparatus is a device that outputs a laser beam having three characteristics of monochromatic, coherence, and collimation, compared to natural light or light radiated from a lamp. The laser beam output from the laser apparatus have a different wavelength and a different pulse width depending on a condition in which the laser beam is generated.

Recently, technologies for treating a human body by modifying a state of a human tissue or removing a tissue by use of light has been widely used. Accordingly, there are efforts to develop therapy apparatuses utilizing various light sources, including a laser beam.

Among them, a laser therapy apparatus has different characteristics of being absorbed into a tissue depending on a wavelength of irradiated light, and polarization properties of the light may affect such characteristics. Thus, in order to select and maintain polarization properties, the laser therapy apparatus may include an optical element, such as a polarization controller and a polarization splitter.

When it comes to generating a laser beam for treatment, the laser therapy apparatus may be configured to allow the laser beam to have polarization properties indicative of dominant p-polarized light or s-polarized light, and maintain the polarization properties. However, in existing technologies, a refractive index is changed because laser alignment, internal temperature of a crystal, or strength of the laser beam is changed in the process of generating a laser beam for treatment, and the change of a reflective index frequently results in switching between the p-polarized light or s-polarized light.

DISCLOSURE

Technical Problem

An object of the present invention is to provide a laser therapy apparatus that is capable of generating a laser beam for treatment with dominant polarization properties by use of a compact optical structure.

In addition, another object of the present invention is to provide a laser therapy apparatus that is capable of maintaining polarization properties of a laser beam by minimizing a possibility that the polarization properties.

Technical Solution

In order to achieve the above object, the present invention provides a laser apparatus including: a plurality of reflection mirrors forming a resonance path so as for light to be amplified by induced emission; a medium having a first surface and a first interface, and configured to amplify and discharge the light by absorbing energy from a light source, wherein the first surface forms a vertical surface with respect to the resonance path and the first interface does not form a vertical surface with respect to the resonance path; and a saturable absorber having a second surface and a second interface, and configured to generate ultrashort pulses, wherein the second surface forms a vertical surface with respect to the resonance path and the second interface does not form a vertical surface with respect to the resonance path.

The first surface defining one cross section of the medium, and the second surface defining one cross section of the saturable absorber may be disposed on one surface of the plurality of reflection mirrors, and the first interface defining the other cross section of the medium, and the second interface defining the other cross section of the saturable absorber may be disposed to oppose each other.

When light travelling along the resonance path is incident onto the first interface or the second interface, the light may be reflected and refracted in directions perpendicular to each other.

A difference between a tilt angle formed by the first interface of the medium and a tilt angle formed by the second interface of the saturable absorber may be in between 0° and 10°.

A predetermined interval may be formed between the first interface of the medium and the second interface of the saturable absorber, and the interval may be a material layer having a refractive index of n=1~1.5.

When the light travelling along the resonance path passes through the first interface or the second interface, loss for the light polarized in one of two directions orthogonal to each other may be reduced.

The light travelling along the resonance path may be emitted at an incident angle of α, which satisfies tan α=n1/n2, so as to discharge a laser beam, wherein a ratio of refractive indexes between the material layer and the saturable absorber is n1:n2.

When the light travelling along the resonance path is incident at Brewster angle relative to the first interface or the second interface, one of polarized lights of two directions included in the light may not be reflected.

The saturable absorber may be in a crystalline structure having first to third crystallographic axes orthogonal to one another, and the light passing through the saturable absorber may have polarized lights in two directions orthogonal to each other, one of the polarized lights which has a polarization transmittivity dominant than the other.

The saturable absorber may be cut so that the light travelling along the resonance path propagates toward a crystallographic axis in a direction <110>.

The medium may be provided as neodymium-doped yttrium aluminum garnet (Nd:Yag), and the saturable absorber may be provided as four-valence Chromium Doped Yttrium Aluminum Garnet (Cr4+:YAG).

The plurality of reflection mirrors may include: a total internal reflection mirror disposed in one side of the medium, and configured to reflect light output from the medium; and an output mirror disposed in one side of the saturable absorber, and configured to output light output from the saturable absorber.

The present invention provides a laser apparatus including: a body; a light source part disposed inside the body, and configured to oscillate a laser beam as light, which causes induced emission, resonates in a medium and a saturable absorber including a specific inclined plane; a light transfer unit connected to the body, and forming a path for a laser beam oscillated by the light source part; and a light emitting unit configured to receive the laser beam from the light transfer unit and emit the laser beam to an outside.

The details of other embodiments are included in the following description and the accompanying drawings.

Advantageous Effects

According to the present invention, a medium or a saturable absorber of a laser therapy apparatus may be designed in consideration of a crystal direction and a tilt angle of a cross section, through which a laser beam passes, and thus, there are effects of generating a laser beam for treatment with excellent polarization properties in one direction and maintaining the polarization properties of the laser beam in the process of generating the laser beam, while preventing switching of the polarization properties.

DESCRIPTION OF DRAWINGS

FIGS. 6A and 6B are a diagram for explanation of a travelling direction of light incident onto a medium and a saturable absorber.

BEST MODE

Hereinafter, a laser apparatus according to an embodiment of the present invention will be described in detail with reference to the accompanying drawings. It should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

Therefore, the description proposed herein is just a preferable example for the purpose of illustrations only, not intended to limit the scope of the disclosure, so it should be understood that other equivalents and modifications could be made thereto without departing from the spirit and scope of the disclosure.

Embodiments of the present invention describe an example of a laser apparatus that treats a human tissue by emitting light onto a skin surface, but the present invention is not limited thereto and may be applied to other various therapy apparatuses for treating a body part other than skin by use of light.

Figure 1:
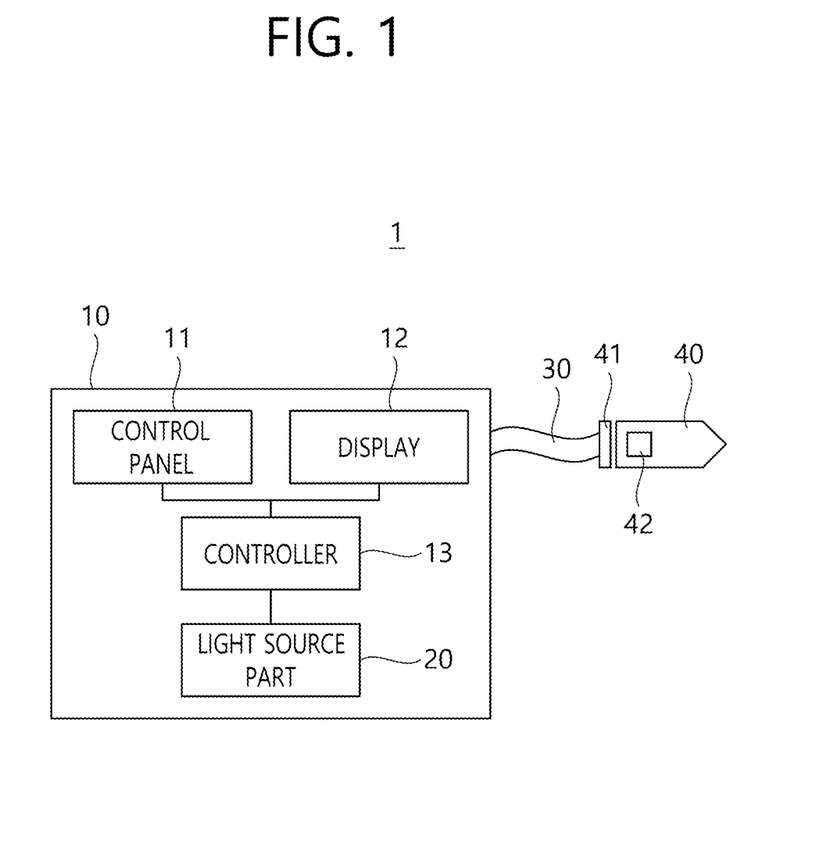
FIG. 1 is a block diagram briefly illustrating a laser apparatus according to an embodiment.

FIG. 1 is a block diagram briefly illustrating a laser apparatus according to an embodiment of the present invention.

Referring to FIG. 1, a laser apparatus 1 according to an embodiment of the present invention includes a body 10, a light source part 20 disposed inside the body 10, a light transfer unit 30 extending from the body 10, and a light emitting unit 40 connected to the light transfer unit 30 and configured to emit a laser beam to the outside.

The body 10 defines the exterior appearance of the laser apparatus 1. The body 10 is designed to be supplied with power from the outside, and include various constituent elements that generate light. Specifically, the light source part 20 configured to oscillate a laser beam, and other various electronic components including a heat radiation part (now shown) are provided inside the body 10. In addition, a control panel 11 for controlling operation of the laser apparatus 1, and a display 12 for displaying a manipulation menu or an ongoing operation to a user are provided on the exterior surface of the body 10. The light source part 20, the control panel 11, the display 12, and any electronic component installed in the body 10 may be controlled by a controller 13.

For example, the light transfer unit 30 may be a cable extending from one outer surface of the body, and the light emitting unit 40 may be connected to a fastening part 41 of a cable end portion. The fastening part 41 of the cable is connected to an end portion of the light emitting unit 40 by screw-fastening or any other combination.

A path along which a laser beam travels is formed inside the light transfer unit 30 installed between the body 10 and the light emitting unit 40. For example, an optical fiber, a signal line, and the like may be provided inside the light transfer unit 30. A laser beam generated inside the body 10 is transferred to the light emitting unit 40 along an optical fiber of the light transfer unit 30. In addition, content controlled by the control panel 11 of the body 10 or a signal controlled by a manipulation unit 42 of the light emitting unit 40 secured to the cable may be transferred along a signal line of the cable. In addition, the signal line is configured to transfer various control signals, which are generated by the control panel 11 of the body or the manipulation unit 42 of the light emitting unit, between the body 10 and the light emitting unit 40.

In the present invention, an example of the cable is described as the light transfer unit 30, but the light transfer unit 30 may be in the structure of a rotatable or bendable arm. Specifically, a bent arm (not shown) having mobility along the X, Y, and Z-axes is connected to the outside of the body 10. The bent arm extends from an outer surface of the body 10 to have mobility along the X, Y, and Z axes. For example, the bent arm has various mobilities, such as orbital motion and reciprocating motion, with respect to the body 10. The bent arm may be in the form of a plurality of links, and may accommodate a transfer member (not shown), such as an optical fiber, which is capable of transferring a laser beam output from the light source part 20.

Meanwhile, the light emitting unit 40 may be in the form of a hand piece which a user can grip with a hand and performs a surgical procedure by changing a holding position. The light emitting unit 40 may include a cooling mechanism to cool the surface of a treatment site. For example, the cooling mechanism may include a cooling gas discharge orifice (not shown). In addition, a manipulation part 41 by which a user is able to manipulate an operation, for example emitting light and discharging cooling gas, may be provided on an outer surface of the light emitting unit 40.

Figure 2:
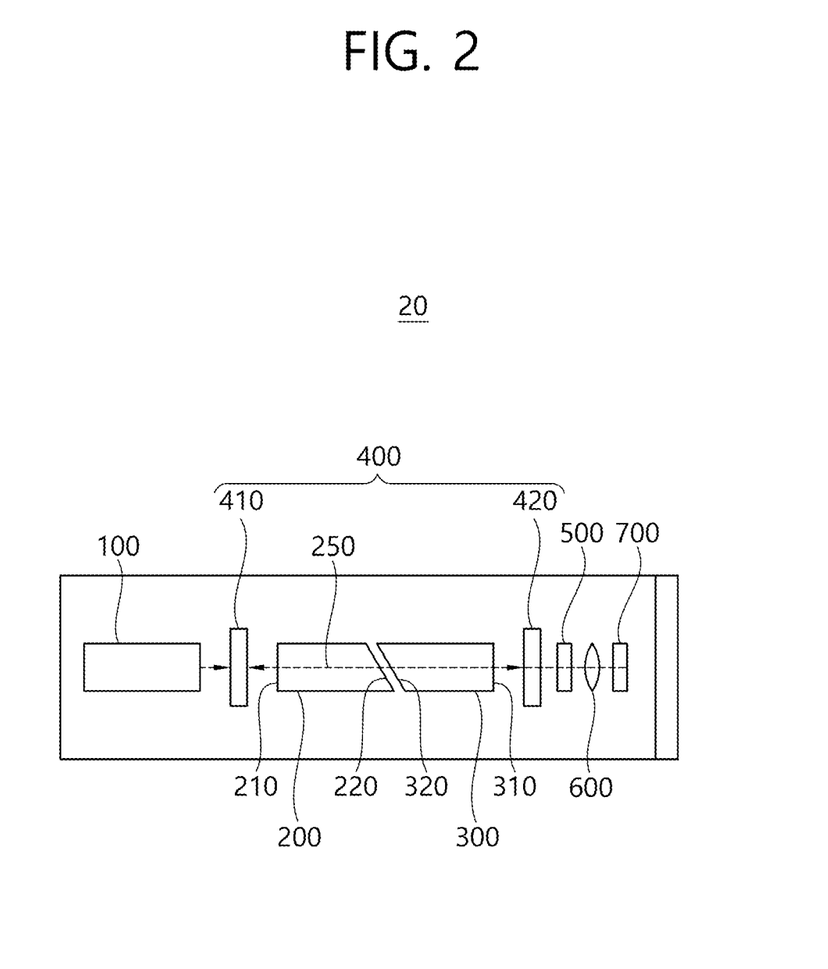
FIG. 2 is a diagram illustrating a light source part shown in FIG. 1 according to an embodiment of the present invention.
Figure 3:
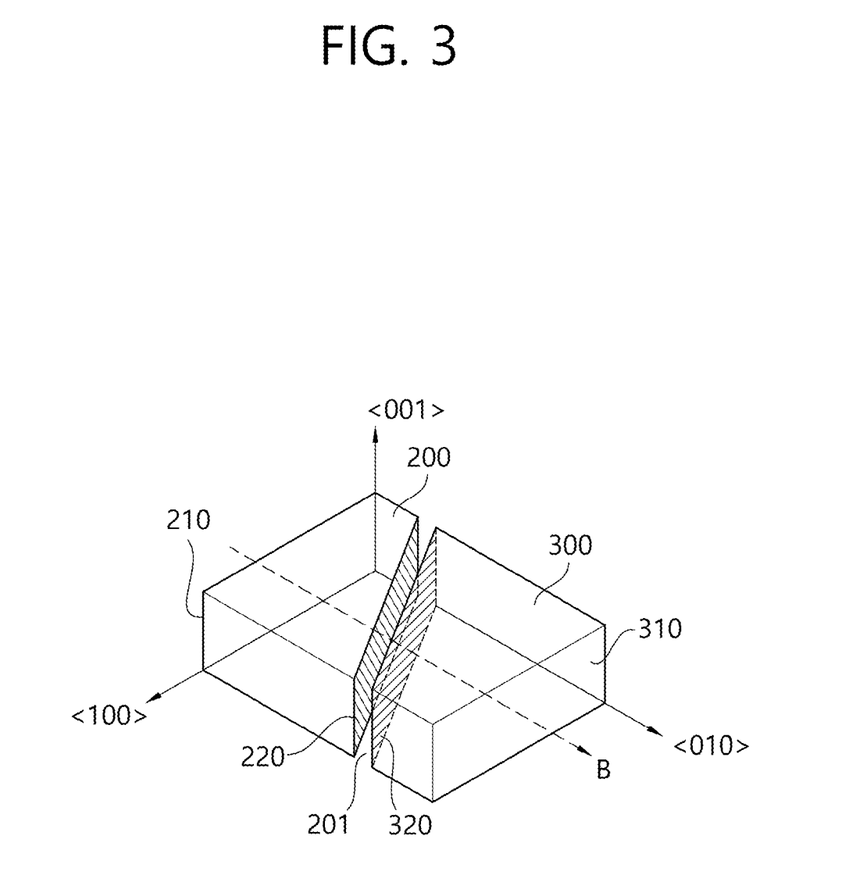
FIG. 3 is a perspective view illustrating a medium and a saturable absorber according to an embodiment of the present invention.

FIG. 2 is a diagram schematically illustrating the light source part shown in FIG. 1 according to an embodiment of the present invention, and FIG. 3 is a diagram illustrating a medium and a saturable absorber according to an embodiment of the present invention.

As illustrated in FIGS. 1 and 2, the body 10 includes the light source part 20 for generating a laser beam. Referring to FIG. 2, the light source part 20 may include a light source 100, a medium 200, a saturable absorber 300, and a reflection mirror 400. In addition, the light source part 20 may further include an optical member, such as a shutter 500 which is disposed in one side of the reflection mirror 400 and disposed along a path of a laser beam, a filter 600, and a lens 700. Although FIG. 2 shows a structure in which the reflection mirror is provided as an additional member, the reflection mirror may be omitted and a reflection layer may be coated on one surface (the left-hand side surface in FIG. 2) of the medium and one surface (the right-hand side surface in FIG. 2) of the saturable absorber. The light source 100 may be a flash lamp, and disposed on a side surface or a rear surface of the medium 200 to generate excitation light necessary to generate a laser beam.

The medium 200 may absorb energy of excitation light generated by the light source 100, and amplifies and discharges light B. The medium 200 according to this embodiment may utilize neodymium-doped yttrium aluminum garnet (Nd:Yag). Thus, the light source part 20 may generate light with a wavelength of 1064 nm, the light which oscillates in Nd:Yag. However, the light source part may be configured to generate lights with various wavelengths using various kinds of mediums in addition to Nd:Yag.

Light generated in the medium 200 travels toward the saturable absorber 300. The saturable absorber 300 may be disposed in one side of the medium 200, and provided as four-valence Chromium Doped Yttrium Aluminum Garnet (Cr4+:YAG). Cr4+:YAG may be a passive Q-switcher for generating picosecond or nanosecond ultrashort pulses.

The saturable absorber 300 may absorb light of intensity smaller than a specific level, and transmit light of intensity equal to or greater than the specific level. A number of pulses fluctuates in the light source 20, and, among them, pulses of intensity equal to or greater than the specific level freely reciprocate in the light source part 20 to thereby grow into laser pulses, without being greatly affected by the saturable absorber 300. However, pulses of intensity smaller than the specific level is absorbed to disappear. Thus, the pulses of intensity equal to or greater than the specific level without being affected by the saturable absorber causes laser oscillation to occur to thereby make a laser beam to be output at specific time intervals through a reflection mirror in one side of the light source part. That is, only pulses adapted to the saturable absorber-included environment to survive may be output as a laser beam.

In the present invention, a pulse of intensity smaller than the specific level may be reflected by the reflection mirror 400 to reciprocate until the pulse grows to have intensity equal to or greater than the specific level.

The reflection mirror 400 is disposed in one side of the medium 200 and in one side of the saturable absorber 300, and forms a path 250 along which a light generated from the medium reciprocates to resonate. Thus, light may be amplified while reciprocating between the medium 200 and the saturable absorber 300 in the reflection mirror 400.

Specifically, if the medium 200 and the saturable absorber 300 are disposed sequentially in the light-to-right direction in the light source part 20, the reflection mirror 400 may be disposed on an outer surface of the medium 200 and on an outer surface of the saturable absorber 300.

The reflection mirror 40 may include a total internal reflection mirror 410 and an output terminal 420. That is, the reflection mirror 400 may include the total internal reflection mirror 410 disposed in one side of the medium 200, and the output mirror 420 disposed in one side of the saturable absorber 300, wherein the total internal reflection mirror 410 reflects light output from the medium 200 and the output mirror 420 is a mirror to which light passing through the saturable absorber 300 is output.

The shutter 500, the filter 600, and the lens 700 are disposed in one side of the output terminal 400 along a travelling direction of a laser beam. The laser beam output through the output mirror 420 travels through the shutter 500, the filter 600, and lens 700. The lens 700 may be a convex lens for condensing laser beams. Light B condensed through the convex lens may travel toward the light emitting unit 40 through the light transfer unit 30.

Meanwhile, the laser apparatus may be configured to oscillate a laser beam so that any one of p-polarization and s-polarization have dominant polarization properties. In this case, the laser apparatus needs to apply polarization properties to a laser beam and form an optical path along which the polarization properties of the laser beam can be maintained constantly.

Thus, the light source part 20 according to the present invention may utilize a saturable absorber cut in a specific crystallographic direction so as to generate light having dominant polarization properties in one direction. Furthermore, in order to maintain the polarization properties of selected light, the saturable absorber may have an inclined plane on which light travels.

Figure 4:
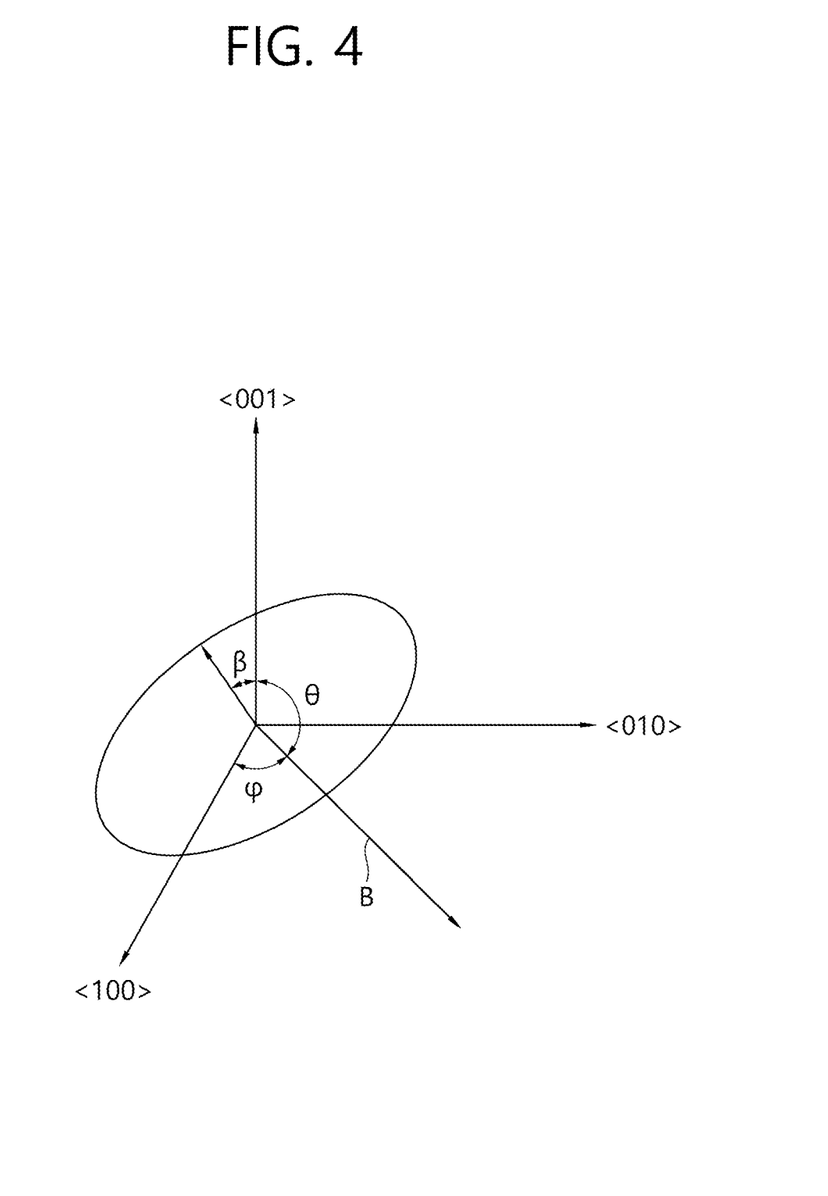
FIG. 4 is a schematic view illustrating alignment of a direction of incidence of light and a crystal direction in a four-valence Chromium Doped Yttrium Aluminum Garnet (Cr4+:YAG) crystal according to an embodiment of the present invention.
Figure 5:
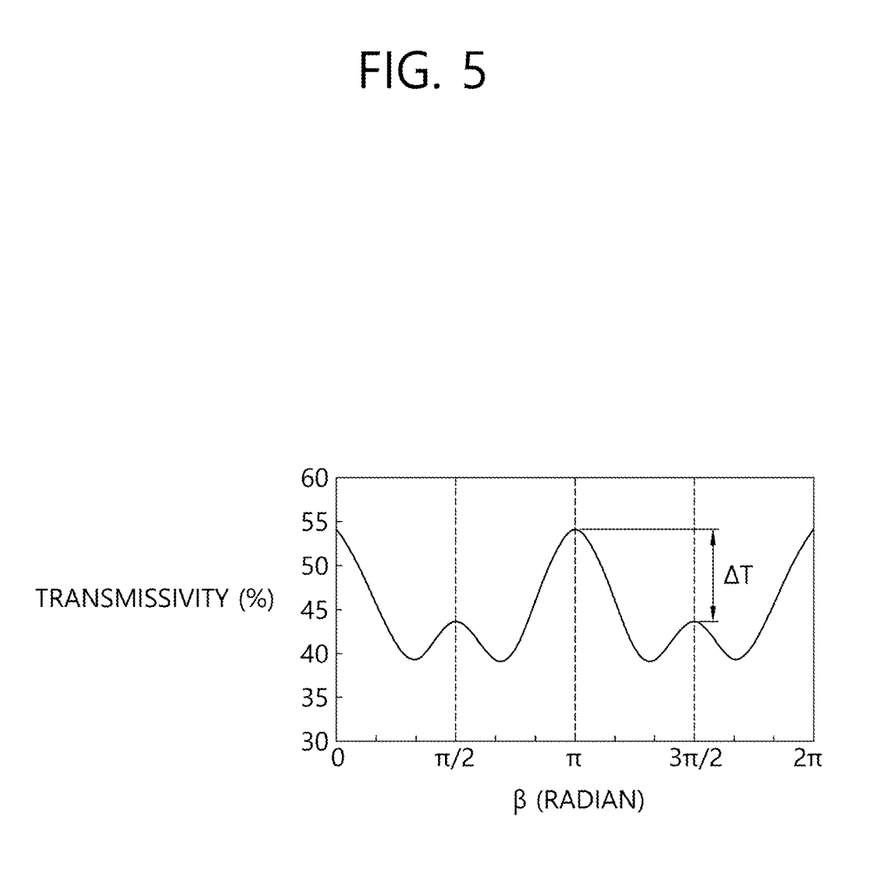
FIG. 5 is a diagram illustrating a transmittivity according to a direction of polarization when light travels along a direction of a crystallographic axis <110> according to an embodiment of the present invention.

Referring to FIGS. 4 and 5, there will be described a crystal direction of the saturable absorber according to an embodiment of the present invention and polarization transmission properties according to a travelling direction of light.

FIG. 4 is a schematic view illustrating alignment of a direction of incidence of light and a crystal axis in a Cr4+:YAG crystal according to an embodiment of the present invention. FIG. 5 is a diagram illustrating a transmittivity according to a direction of polarization when light travels along a direction of a crystallographic axis <110> according to an embodiment of the present invention.

As illustrated in FIG. 4, the saturable absorber 300 according to an embodiment of the present invention is formed in a crystalline structure having first to third crystallographic axes orthogonal to one another. Specifically, the first crystallographic axis may be <001>, the second crystallographic axis may be <100>, and the third crystallographic axis may be <010>.

In this case, the saturable absorber 300 may have different transmission properties of each polarized light according to a travelling direction of light with respect to a crystallographic axis. Thus, as the saturable absorber is configured to have a great transmittivity deviation between polarized lights in two directions (p-polarized light and s-polarized light) orthogonal to each other, it is possible to oscillate a dominant polarized light in one direction.

As illustrated in FIG. 4, when a direction of light is set as direction B, a first angle between a first crystallographic axis of the saturable absorber 300 and an axis of light B corresponding to a resonance path of the light source part 20 may be θ, whereas a second angle between a shadow of the light B and the second crystal axis on a plane including a second crystallographic axis and a third crystallographic axis may be φ.

In addition, as an example of an embodiment of the present invention, when a direction of light is φ of π/4 (the first angle) and θ of π/2 (the second angle), it is found that the light has dominant polarization transmission properties in one direction. That is, when the saturable absorber 300 is cut so that a travelling direction of light is toward the crystal axis <110>, the direction of light may have the above-suggested first and second angles, and the light B passing through the saturable absorber 300 may show dominant polarization in one direction.

FIG. 5 is a graph showing a transmittivity according to polarization properties of light when the light travels in a direction shown in FIG. 4. As illustrated in FIG. 4, if light passes in the crystal direction <110> of the saturable absorber, polarization properties according to a direction of polarization β of the light has a maximum value when the direction of polarization β is 0, π, and there is a transmittivity difference as much as ΔT with respect to the direction of polarization β which is π/2 from a point having the maximum value.

Thus, in this embodiment, it is possible to configure an optical path having a transmittivity difference between p-polarized light and s-polarized light by using transmission properties according to a crystal direction of the saturable absorber. Accordingly, when passing through the saturable absorber, light generated by the light source part 20 may be processed so that the p-polarization has dominant properties compared to the s-polarization.

However, as described above, although the saturable absorber 300 is disposed so that the light B travels toward a crystal direction in a direction <110>, a birefringence may be very small and thus the p-polarization and the s-polarization may be switched. Specifically, if the birefringence is small, polarization may be switched due to change of a refractive index which is caused by change of the laser alignment, change of crystal temperature, or change in strength of a laser beam.

Thus, in this embodiment, a cross section onto which light is incident from the medium 200 or to which light is output from the saturable absorber 300 may be in the form of an inclined plane so as to maintain polarization properties of light. Hereinafter, the structure of the medium and the saturable absorber will be described in more detail.

Referring to FIGS. 2 and 3, the medium 200 and the saturable absorber 300 may be aligned in the light source part 20, and a first surface 210 of the medium 200, a first interface 220 of the medium 200, a second interface 320 of the saturable absorber 300, and a second surface 310 of the saturable absorber 300 may be disposed sequentially in the left-to-right direction. Thus, as described above, the light B reciprocates so as to resonate and be amplified while passing through the medium 200 and the saturable absorber 300 between reflective mirrors positioned on both sides, and a laser beam reaching to a specific level of energy may be discharged from the light source part 20 through the reflection mirror 400. The laser beam output from the medium 200 and the saturable absorber 300 may travel toward the light transfer unit 30 and the light emitting unit 40, as described above.

In addition, the first interface 220 of the medium 200 and the second interface 320 of the saturable absorber 300 may be disposed at a specific interval. A material layer 201 may be disposed in the interval, and thus, the medium 200, the material layer 201, and the saturable absorber 300 may be aligned sequentially in a broad sense. The material layer 201 may be formed of a material having a reflective index of n=1~1.5: for example, if n=1, the material layer 201 may be an air layer.

Specifically, in the structure of the medium 200, the first surface 210 defining one cross section in a direction toward the reflection mirror 410 may be disposed perpendicular to the resonance path 250, and the first interface 220 defining the other cross section may be disposed with a specific angle, rather than being perpendicular, relative to the resonance path 250.

In the structure of the saturable absorber 300, the second interface 320 defining one cross section in a direction toward the medium 200 may be disposed on the first interface 220 of the medium 200 with a specific gradient, and that the second surface 310 defining the other cross section in a direction toward the reflection mirror 420 of the saturable absorber 300 may be disposed perpendicular to the resonance path 250.

In addition, a tilt angle formed by the first interface 220 of the medium 200 of the light source part 20 and a tilt angle formed by the second interface 320 of the saturable absorber 300 may be identical to form a parallel plane or may be different within 10°. The first interface 220 and the second interface 320 may form an inclined plane having the aforementioned tilt angle while opposing each other.

Due to the above structure, the light B travelling along the resonance path 250 may pass through the first interface 220 of the medium 200 and the second interface 320 of the saturable absorber 300.

Here, according to a tilt angle formed by the first interface 220 or the second interface 320, the medium 200 or the saturable absorber 300 may reduce loss for polarized light in one of two directions (p-polarized light and s-polarized light) of the light B passing through the first interface 220 or the second interface 320. For example, in this embodiments, the first interface 220 or the second interface 320 is formed to have a specific tilt angle so as to maintain polarization properties of light (the properties which indicate dominance of p-polarization).

Specifically, in this embodiment, the medium 200 may be Nd:YAG, the saturable absorber 300 may be Cr4+:YAG, and a tilt angle of the first interface 220 or the second interface 320 may be between 60° to 65°. In this case, oscillation of the aforementioned p-polarization which is selected for dominance polarization transmission properties may be maintained.

Figure 6A:
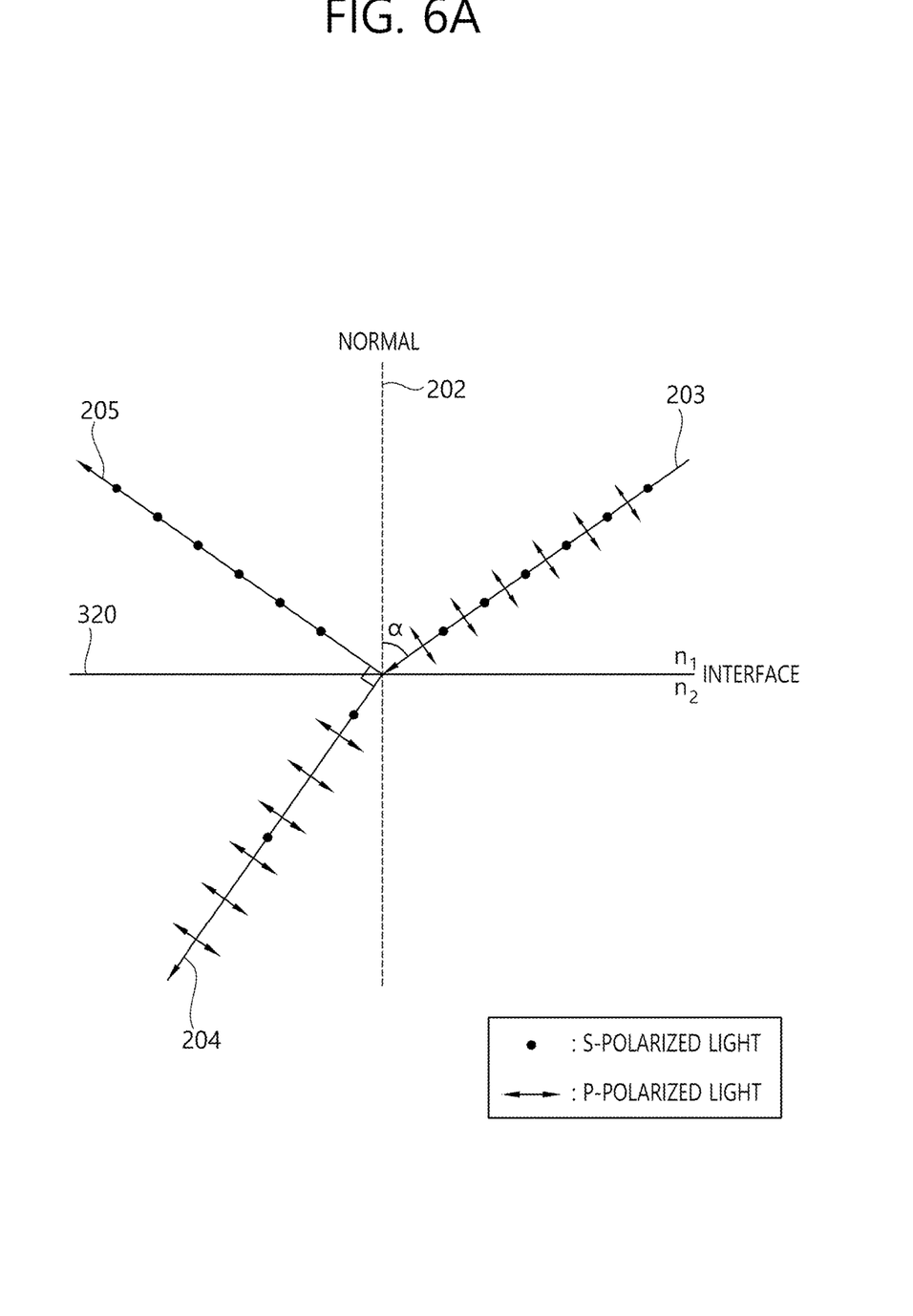
FIG. 6A is a diagram illustrating light having polarization components in two directions, the light which is incident at a specific incident angle.
Figure 6B:
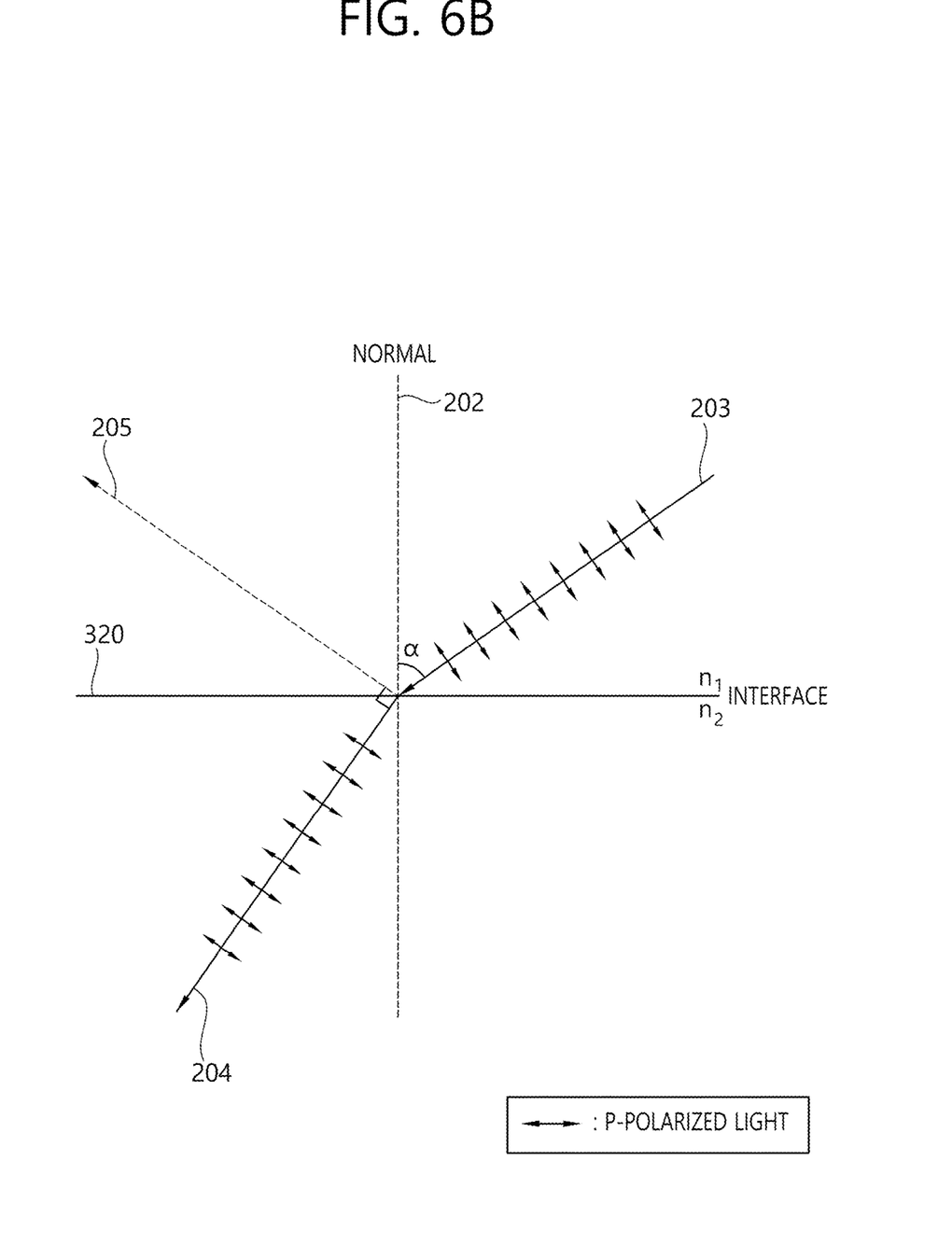
FIG. 6B is a diagram illustrating light having a polarization component in one direction, the light incident at a specific incident angle.

Hereinafter, there is detailed description about a tilt angle of an interface of a medium or a saturable absorber, and polarization properties of light passing through the interface. FIG. 6 is a diagram illustrating a travelling direction of light incident onto a medium or a saturable absorber, and the following description is provided mainly about a tilt angle of the second interface 320 of the saturable absorber 300 for convenience of explanation.

Specifically, FIG. 6A is a diagram illustrating the case where light having polarization components in two directions is incident at a specific incident angle, and FIG. 6B is a diagram illustrating the case where light having a polarization component in one direction is incident at a specific incident angle.

Generally, if light is incident between two different mediums having different refractive indexes, some of the light is refracted and the rest of the light is reflected. At this point, if the light is incident at a specific incident angle onto interfaces of the two mediums, reflection and refraction occurs in directions perpendicular to each other. The specific incident angle is called Brewster angle or a polarizing angle.

FIG. 6A shows the case where light is incident at an incident angle of α onto the second interface 320 of two mediums (which are the material layer 201 and the saturable absorber 300 in the present invention), wherein a ratio of refractive indexes between the two mediums is n1:n2. If tan α=n1/n2 is satisfied, light 204 refracted from the second interface 320 and light 205 reflected from the second interface 320 travel in directions perpendicular to each other, and the reflected light 205 is reflected in a polarized state in which the light 205 oscillates in a specific one direction.

Generally, when refraction and reflection of light occurs after the light is incident between two mediums (which are the material layer 201 and the saturable absorber 300 in the present invention), s-polarized light oscillating in a direction perpendicular to a plane of incidence is reflected strongly more than a p-polarized light oscillating in a direction parallel to the plane of incidence with respect to most of incident angles.

In particular, as in the present invention, when light 203 is incident at a specific incident angle (for example, Brewster angle), most of p-polarized light oscillating in a direction parallel to a plane of incidence is not reflected but refracted.

Thus, the light 205 reflected from the second interface 320 has few p-polarized light and has only s-polarized light oscillating in a direction perpendicular to the plane of incidence (which is, in this case, a plane including the incident light 203, the reflected light 205, and the normal 202). In addition, the light 204 refracted from the second interface 320 has more dominant p-polarization properties, compared to the incident light 203.

FIG. 6B shows the case where incident light is incident at an incident angle of α (in this case, tan α=n1/n2) onto the second interface 320 of two mediums (which are the material layer 201 and the saturable absorber 300 in the present invention). A travelling path of the light 204 refracted from the second interface 320 and a travelling path of the light 205 reflected from the second interface 320 are perpendicular to each other: in this case, if the incident light 203 is p-polarized light, the incident light 203 is not reflected. Because the incident light 203 is incident onto the second interface 320 in a p-polarized state which indicating a magnetic field oscillating in a direction parallel to the plane of incidence, the incident light 203 in the p-polarized state is all refracted and not reflected.

Thus, according to an embodiment of the present invention, when light passing through the first interface 220 of the medium 200 is incident onto the second interface 320 of the saturable absorber 300, the light may be incident at Brewster angle. The incident light 203 having Brewster angle is formed to be reflected and refracted at angles perpendicular to each other, and the p-polarized light oscillating in a direction parallel to the plane of incidence is not reflected but refracted.

Thus, the light reflected from the second interface 320 does not have the p-polarized light but has only the s-polarized light which oscillates in a direction perpendicular to the plane of incidence. That is, light passing through the second interface 320 may increase loss for s-polarization.

Thus, the light B travelling along a resonance path in the light source part 20 is emitted at an incident angle of α, which satisfies tan α=n1/n2, with respect to the material layer 201 and the saturable absorber 300 to thereby discharge a laser beam, wherein a ratio of refractive indexes between the material layer 201 and the saturable absorber 300 is n1:n2. Due to the incidence of the light at the incident angle, Brewster angle is formed relative to the second interface 320 between the material layer 201 and the saturable absorber 300, and one polarized light is not reflected from the second interface 320. The polarized light which is not reflected may be p-polarized light.

As such, the laser apparatus according to an embodiment of the present invention may be configured such that light passing through an saturable absorber have dominant p-polarization properties by use of a direction of a crystal axis of the saturable absorber and a direction of incidence of the light. Furthermore, by using a tilt angle of an interface of a medium and/or the saturable absorber through which the light passes, the laser apparatus may constantly maintain light having dominant p-polarization properties or may make p-polarization properties more dominant.

Although embodiments of the present invention have been described for illustrative purposes, the present invention is not limited to the above-described specific embodiments, and those of ordinary skill in the art to which the present invention pertains will appreciate various changed in form and detail may be made therein without departing from the spirit and scope of the invention as defined by the appended claims. Thus, the aforementioned embodiments should be understood as exemplary and non-limiting. The scope of the present disclosure is defined by the following claims rather than by the detailed description of the embodiment. It shall be understood that all modifications and embodiments conceived from the meaning and scope of the claims and their equivalents are included in the scope of the present disclosure.

The invention claimed is:

1. A laser apparatus comprising:
   a plurality of reflection mirrors forming a resonance path so as for light to be amplified by induced emission;
   a medium having a first surface and a first interface, and configured to amplify and discharge the light by absorbing energy from a light source, wherein the first surface forms a vertical surface with respect to the resonance path and the first interface does not form a vertical surface with respect to the resonance path; and
   a saturable absorber provided as four-valence Chromium Doped Yttrium Aluminum Garnet (Cr4+:YAG), having a second surface and a second interface, and configured to generate ultrashort pulses, wherein the second surface forms a vertical surface with respect to the resonance path and the second interface does not form a vertical surface with respect to the resonance path,
   wherein the saturable absorber is in a crystalline structure having first to third crystallographic axes orthogonal to one another and is cut so that the light traveling along the resonance path propagates toward a crystallographic axis in a direction <110> so that a transmittivity of p-polarization is dominant than a transmittivity of s-polarization, and
   wherein the first interface and the second interface are configured so that a reflection of s-polarized light is more dominant than a reflectance of p-polarized light so as to maintain a polarization property of the light even though a polarization switching occurs.

2. The laser apparatus of claim 1,
   wherein the first surface defining one cross section of the medium, and the second surface defining one cross section of the saturable absorber are disposed on one surface of the plurality of reflection mirrors, and wherein the first interface defining the other cross section of the medium, and the second interface defining the other cross section of the saturable absorber are disposed to oppose each other.

3. The laser apparatus of claim 1, wherein, when light travelling along the resonance path is incident onto the first interface or the second interface, the light is reflected and refracted in directions perpendicular to each other.

4. The laser apparatus of claim 1, wherein a difference between a tilt angle formed by the first interface of the medium and a tilt angle formed by the second interface of the saturable absorber is in between 0° and 10°.

5. The laser apparatus of claim 1, wherein a predetermined interval is formed between the first interface of the medium and the second interface of the saturable absorber, and the interval is a material layer having a refractive index of n=1-1.5.

6. The laser apparatus of claim 3, wherein the light travelling along the resonance path is emitted at an incident angle of a, which satisfies tan α=n1/n2, so as to discharge a laser beam, wherein a ratio of refractive indexes between the material layer and the saturable absorber is n1:n2.

7. The laser apparatus of claim 3, wherein, when the light travelling along the resonance path is incident at Brewster angle relative to the first interface or the second interface, one of polarized lights of two directions included in the light is not reflected.

8. The laser apparatus of claim 1, wherein the medium is provided as neodymium-doped yttrium aluminum garnet (Nd:YAG).

9. The laser apparatus of claim 1, wherein the plurality of reflection mirrors comprises:
- a total internal reflection mirror disposed in one side of the medium, and configured to reflect light output from the medium; and
- an output mirror disposed in one side of the saturable absorber, and configured to output light output from the saturable absorber.

* * * * *